United States Patent [19]

de Jonckheere

[11] Patent Number: 4,762,582
[45] Date of Patent: Aug. 9, 1988

[54] CONTINUOUS PROCESS FOR THE MANUFACTURE OF DISPOSABLE DIAPERS

[75] Inventor: Raphael de Jonckheere, Bondue, France

[73] Assignee: Boussac Saint Freres B.S.F., Lille, France

[21] Appl. No.: 810,828

[22] Filed: Dec. 18, 1985

Related U.S. Application Data

[63] Continuation of Ser. No. 592,484, Mar. 23, 1984, abandoned.

[30] Foreign Application Priority Data

Mar. 25, 1983 [FR] France ............... 83 04988

[51] Int. Cl.$^4$ ............... A41B 13/02; A61F 13/16
[52] U.S. Cl. ............... 156/164; 156/178; 156/229
[58] Field of Search ............... 156/164, 229, 259, 265, 156/495, 494, 271, 303, 178, 324, 361, 297, 519, 554, 436, 582, 549; 118/420; 226/31, 122

[56] References Cited

U.S. PATENT DOCUMENTS

| | | | |
|---|---|---|---|
| 2,250,209 | 7/1941 | Shoults et al. | 226/31 |
| 2,529,161 | 11/1950 | Kelling et al. | 226/31 X |
| 2,813,506 | 11/1957 | Johnston | 156/549 X |
| 3,336,901 | 8/1967 | Dauchert | 118/420 |
| 4,239,578 | 12/1980 | Gore | 156/164 X |
| 4,261,782 | 4/1981 | Teed | 156/164 X |
| 4,293,367 | 10/1981 | Klasek et al. | 156/494 |
| 4,333,782 | 6/1982 | Pieniak | 156/164 |
| 4,371,417 | 2/1983 | Frick et al. | 156/495 |
| 4,417,935 | 11/1983 | Spencer | 156/164 X |
| 4,464,217 | 8/1984 | Dickover et al. | 156/164 |
| 4,540,610 | 9/1985 | Conklin et al. | 118/420 X |
| 4,626,305 | 12/1986 | Suzuki et al. | 156/164 |

FOREIGN PATENT DOCUMENTS

| | | | |
|---|---|---|---|
| 0027303 | 4/1981 | European Pat. Off. | |
| 0048010 | 3/1982 | European Pat. Off. | |
| 2415433 | 8/1979 | France | |
| 57-46869 | 3/1982 | Japan | 156/259 |
| 2078811 | 1/1982 | United Kingdom | |
| 2118021 | 10/1983 | United Kingdom | |

Primary Examiner—Michael Ball
Assistant Examiner—Ramon R. Hoch
Attorney, Agent, or Firm—Owen, Wickersham & Erickson

[57] ABSTRACT

Continuous process for the manufacture of disposable diapers having an absorbent pad fixed inside a moisture-impermeable envelope. There are front and back transverse margins and a central crotch zone provided with lateral cut-outs to let the legs through. An elastic strand is fixed to the impermeable envelope by adhesion, at least in the crotch zone, and brought into contact with the inner face of the impermeable envelope while continuously driven by a smooth-surfaced rotary drum. The elastic strands are coated with adhesive throughout their length, and the tension exerted on them at the points of contact with the impermeable envelope is made to vary between a value approaching zero, corresponding to the portions of the elastic strands adhered onto the front and back transverse margins, and a maximum value corresponding to the portions of the elastic strands adhered onto the central crotch zone.

10 Claims, 5 Drawing Sheets

CONTINUOUS PROCESS FOR THE MANUFACTURE OF DISPOSABLE DIAPERS

This application is a continuation of application Ser. No. 592,484, filed Mar. 23, 1984.

The object of this invention is a process for manufacturing disposable diapers and also the diapers or diaper briefs so obtained. It is known that disposable diapers, which are used for young infants as well as for incontinent adults, comprise as the main elements in integrated form: a flexible impermeable outer envelope acting as the brief and an absorbent pad fixed inside the impermeable envelope, which pad may be covered with an inner liner permeable to moisture. Such a diaper brief or disposable diaper makes it possible to replace both the traditional absorbent diaper and the impermeable briefs which are used in combination with the said diaper.

In order to improve the leaktightness of the diapers at the crotch it has already been planned to place elastic elements along the cut-outs made for the legs to pass through in the impermeable outer envelope acting as the briefs (see, for instance, Amer. U. S. Pat. Nos. 3,860,003 and 4,050,462).

The straight elastics have so far been fixed by gluing inside the impermeable envelope under constant tension, with the gluing being performed intermittently, on the other hand, so that only the section of the elastics corresponding to the crotch zone is fixed by adhesive onto the continuously travelling thin sheet designed to form the impermeable outer envelope of each of the diaper briefs after cutting out. The last step in the manufacturing process consists in then cutting across the continuous strip forming the sheet designed to form the impermeable outer envelope carrying the suitably attached absorbent pads, as well as an inner permeable liner if need be, adhesive fixing tabs and also the elastics which have just been mentioned. During this cutting operation the ends of these elastics which have not been adhered onto the inner face of the impermeable sheet retract inside the diaper brief itself. So that a diaper is finally obtained with the crotch zone comprising, on each side of the absorbent pad, elastic means under strong tension which cause gathers to form and the effect of this, as has been observed in practice, is to improve the leaktightness of the crotch zone. On the other hand the front and back margins of the diaper are without such gathers, which makes the diaper easier to fit and easier to close round the waist region.

However, this classic process has the drawback of leaving the retracted ends of the elastics visible and of requiring a relatively complex control of the adhesive feed, since this feed must be of intermittent type.

The object of this invention is a new manufacturing process which frees the manufacturer of the difficulties encountered in practice in the classic process.

The process according to the invention provides for the manufacture of disposable diapers comprising an abosrbent pad fixed inside a moisture-impermeable envelope having front and back transverse margins and a middle crotch zone provided with side cut-outs to let the legs through and elastic means fixed to the impermeable envelope by gluing, at least in the crotch zone. The process consists in contacting the said elastic means with the inner face of a sheet designed to form the impermeable envelope driven continuously by a smooth-surfaced rotary drum. According to the invention the continuously fed elastic means are coated with adhesive throughout their length and the tension exerted on the said elastic means is varied periodically at the points of contact with the impermeable envleope from a value close to zero corresponding to the portions of the elastic means glued onto the front and back transverse margins up to a maximum value corresponding to the portions of the elastic means glued on the middle crotch zone.

For the implementation of the process of the invention elastic strips can be used which receive on one of their faces a high-temperature liquid adhesive (hot melt) deposited continuously according to the process of the invention. It is also possible to use a plurality of individual elastic strands which are obtained by continuous separation from a multistrand elastic tape. Each individual strand is then continuously coated all round with a high-temperature liquid adhesive (hot melt). For further details on the implementation of this type of system of individual elastic strands reference may be made to the French patent application No. 83 00780 filed on Jan. 19, 1983 by this applicant.

In all cases the feed of each of the elastic means is preferably by means of a rotary feed roller made of rubber, for example, and grooved if necessary, driven at variable speed and engaging with a friction roller which comes into contact with the feed roller, preferably under the effect of the friction roller's weight.

The surface of the rotary drum driving the impermeable sheet is preferably kept at a temperature of between 30° C. and 100° C. so as to lead to immediate setting of the liquid adheisve carried by each elastic means as soon as the said elastic means comes into contact with the impermeable sheet. The temperature may be maintained either by specific means which may comprise circulation of cooling liquid or simply by using a drum of sufficient mass. The choice of the rotary drum temperature can be easily made by the technician taking into account the parameters of the drum mass, the mass of adhesive per unit length for each of the elastic means, the temperature of the adhesive at the time of contact and also the kind of adhesive. In practice it is observed that a temperature difference of at least 20° C. is needed, and preferably of 70° C. to 130° C., between the adhesive laid on in the liquid state and the outer surface of the rotary drum in order to obtain the required effect of virtually immediate adhesion.

In the installation allowing application of the process of the invention, the continuous feed means for the elastics are placed as close as possible to the rotary drum and work with a variable speed unit controlled so as to periodically modify the tension of the elastics. The glue coating means are installed downstream from the elastic feed means and operate without stopping. It will be understood thus that the elastic means are coated with adhesive continuously whilst their tension varies according to the drive to the feed means variator system.

The speed variation of the feed means can be produced by using any suitable device controlled in accordance with the angular position of the rotary drum round which the impermeable sheet is wound.

In particular feed rollers can be used which are mounted on a shaft which is connected by two gear trains having different gear ratios to a drive shaft through two controlled clutches. A rotary drum angular position sensor connected to the control device supplies signals designed to control the two clutches. In this way it is possible to obtain unstretched elastic portions and suitably stretched elastic portions, with the elongation being as much as 300% or even 400% depending on the elastics used.

Another possibility consists in using feed rollers mounted on a shaft driven by a stepping motor. This stepping motor is controlled by photoelectrically-read encoding disc or similar, having round the periphery thereof two segments with differently spaced lines and driven at constant speed.

Another object of this invention is disposable diaper or diaper brief produced by application of the invention. This disposable diaper comprises an absorbent pad fixed inside a moisture impermeable envelope. The envelope comprises front and back transverse margins and a middle crotch zone provided with side cut-outs to allow the legs to pass through. Elastic means are fixed to the impermeable envelope by gluing at least in the crotch zone. The elastic means comprise a centre portion adhered with tension onto the middle crotch zone and two end portions adhered without tension onto the front and back transverse margins of the envelope.

The invention will be more clearly understood on studying two specific embodiments described as non-restrictive examples and illustrated in the appended drawings in which.

Figure 1:
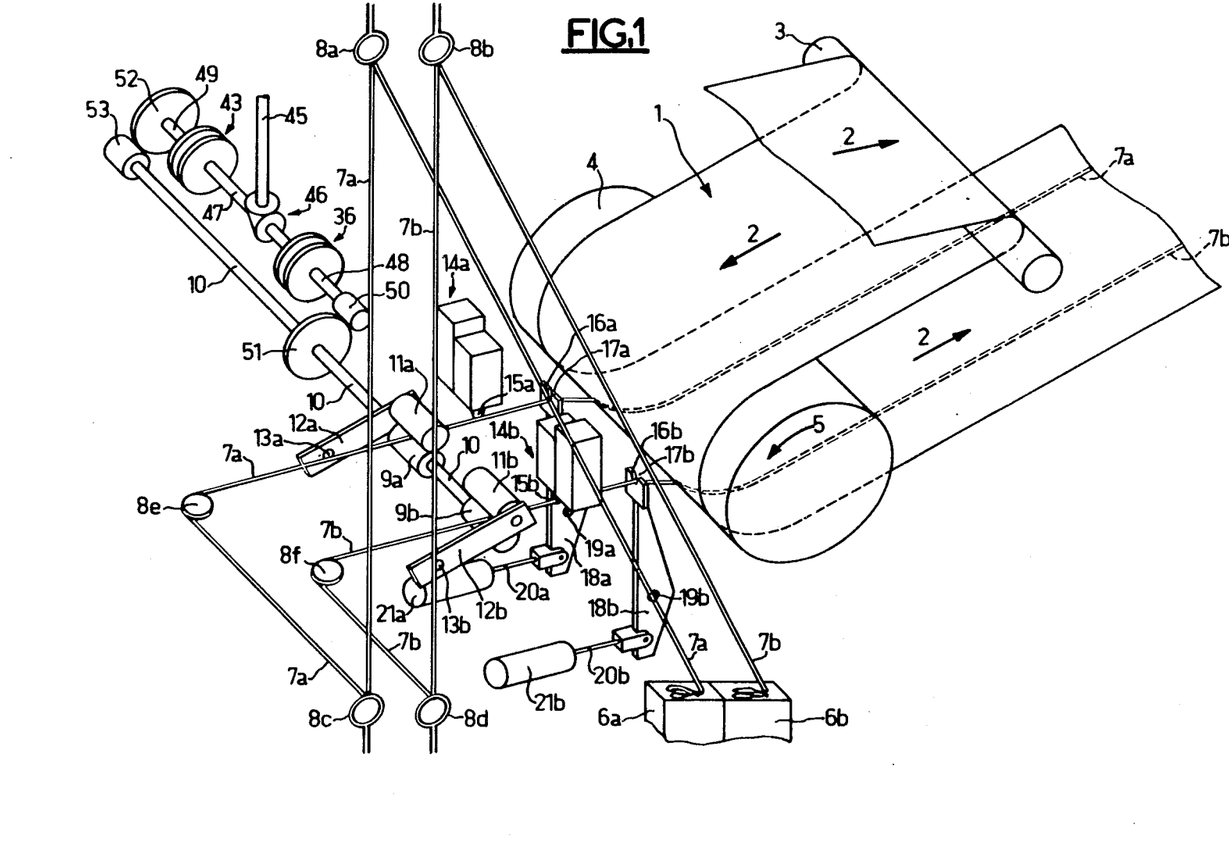
FIG. 1 is a schematic perspective view of a part of an installation permitting implementation of the process of the invention designed for using an elastic strip.

As can be seen in FIG. 1, a thin impermeable sheet 1 is continuousluy unwound in the direction of the arrows 2 passing over a set of rolls, one of which, 3, can be seen in the figure and a rotary drum 4, on the peripheral surface of which this sheet is held throughout a path distance which corresponds roughly to half the circumference of the drum 4. The thin flexible sheet 1 is made of moisture impermeable heat weldable material like polyethylene. The drum 4 is driven in rotation in the direction of the arrow 5 and its smooth outer surface is kept at a relatively low temperature of between 30° C. and 100° C. This temperature can be held by forced artificial cooling inside the drum 4 or simply as shown in FIG. 1 by using a metal drum of sufficient mass.

On the side of the machine are two bins 6a and 6b. Inside each of these bins there is an elastic strip 7a, 7b stowed loose in short successive folds laid on top of each other in layers which are also successive; so that it is possible by pulling on the upper free end of the strip 7a, 7b to withdraw the whole of the strip contained in the bin 6a, 6b without the risk of knots or accumulations forming which might hinder the feed. The elastic strips 7a, 7b coming from their bin 6a, 6b firstly pass through two first guide rings 8a, 8b located approximately above the bins 6a, 6b and above the machine as a whole. The elastic strips 7a, 7b then come back down to the two second guide rings 8c, 8d. The path of the two elastic strips 7a, 7b between the bin 6a, 6b on the one hand and the two respective guide rings 8a, 8b, 8c, 8d on the other hand allows withdrawal of the elastic strips to be controlled without exerting any apprecialbe tension on them. Any loops which might still form at the exit from bins 6a, 6b are eliminated during the journey to the first guide rings 8a, 8b or by passing through these guide rings.

On leaving rings 8c, 8d the two elastic strips 7a, 7b are sent in a direction transverse to the longitudinal axis of the machine. They then travel over weels 8e, 8f which change their direction by 90° and on leaving which the two elastic strips 7a, 7b are parallel to the longitudinal axis of the machine and are separated by a distance which corresponds to their final spacing after being adhered to the sheet 1.

Since the machine is symmetrical round its longitudinal axis, all the parts thereof located on one side of the axis and designated by the letter a will now be described. The symmetrical parts situated on the other side of the axis are identical, can be seen in FIG. 1 and are labelled with the letter b.

The strip 7a passes between a rotary feed roller 9a fixed to a shaft 10 which also carries roller 9b and a friction roller 11a which can rotate freely on its shaft which is carried by a lever 12a able to pivot round a fixed pin 13a. The drive roller 9a may have grooves on it, now shown in the figure, to increase its roughness. The friction roller 11a is located above the feed roller 9a so that the friction roller 11a bears with its own weight against the roller 9a. The elastic strip 7a is thus pinched between the feed roller 9a and the friction roller 11a. In these conditions the elastic strip 7a, as it passes between the feed roller 9a and the friction roller 11a, is travelling at a linear speed which corresponds to the rotational speed of the shaft 10 carrying the feed rollers 9a, 9b.

Immediately downstream of the feed roller 9a an adhesive coating device 14a is installed which comprises a nozzle 15a capable of extruding a stream of high-temperature liquid adhesive (hot melt) directly onto the face of the elastic strip 7a travelling underneath the said nozzle 15a. The face of the adhesive strip 7a is held horizontally, as can be seen in FIG. 1, because of the position of the feed roller 9a.

The elastic strip 7a which is thus coated with adhesive, throughout its length and continuously, then travels over a guide plate 16a provided with a groove 17a and installed on the end of a roughly vertical lever 18a which can pivot round a fixed pivot pin 19a when operated by the rod 20a of a ram cylinder 21a. By pivoting the levers 18a, 18b towards the drum 4 the elastic strips 7a, 7b can be separated from the adhesive dispensing nozzles 15a, 15b during machine stoppages.

The elastic strip 7a is diverted slightly downwards in a vertical plane after it has passed through the guide groove 17a before its upper face coated with liquid adhesive comes into contact with the outer face of the thin sheet 1 wound round the drum 4.

In FIG. 1 the distance between the feed rollers 9a, 9b and the rotary drum 4 has been exaggerated in order to improve clarity. In reality this distance is cut down to a minimum in order to limit as much as possible any absorption of the tension changes in the elastic strip 7a, 7b created by the speed changes of the feed rollers 9a, 9b.

As soon as it comes into contact with the sheet 1 the liquid adhesive carried by each of the elastic strips 7a, 7b sets almost instantly owing to the temperature difference between the liquid adhesive laid hot by the nozzles 15a, 15b and the sheet 1 which is at roughly the same temperature as the periphery of the rotary drum 4 kept at a relatively low temperature, either by internal circulation of a cooling liquid or simply by the size of its metal mass. In these conditions, as soon as they come into contact with the sheet 1, which is travelling at high speed in the direction of the arrows 2, the elastics 7a, 7b are fixed by adhesive onto the said sheet 1. A difference in linear speed between the said sheet 1 and the feed of the elastic strips 7a, 7b by the two feed rollers 9a, 9b produces a tension in the elastic strips 7a, 7b. This tension is produced by an appropriate deceleration of the speed of rotation of the feed rollers 9a, 9b. On the other hand, when the rotational speed of these rollers 9a, 9b is increased in suitable proportions so that the linear speed of the elastic strips 7a, 7b on leaving the feed devices is equal to the linear speed of the sheet 1 wound round the drum 4 the elastic strips 7a, 7b are glued onto the sheet 1 without any tension.

Figure 2:
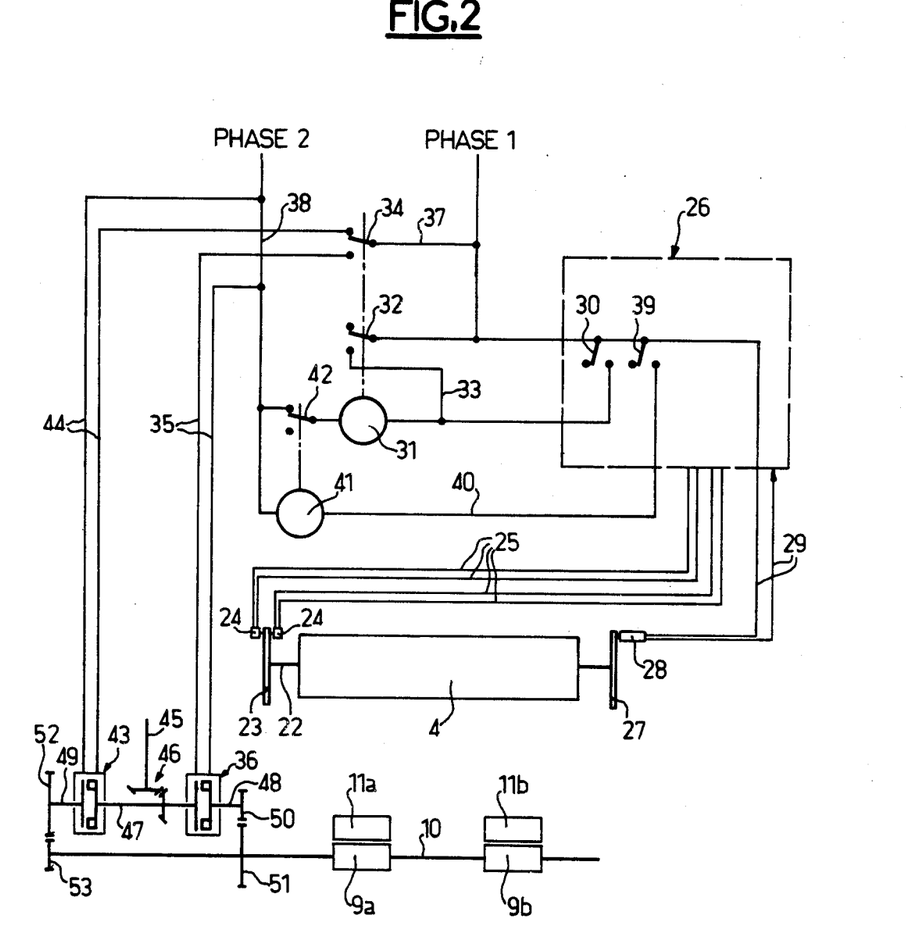
FIG. 2 shows schematically a control device which can be used to vary the tension of the elastics used in the process according to the invention.

FIG. 2, in which the same components carry the same reference numbers, illustrates an embodiment of the means of varying the rotational speed of the feed rollers 9a, 9b carried by the shaft 10.

In FIG. 2 we find the rotary drum 4 carried by its shaft 22 and having on one of its ends an encoding disc 23 possessing a plurality of markings; these pass in front of sensors 24 and each time produce a pulse which is transmitted via connections 25 to a counting system 26. At the other end the shaft 22 carries a second encoding wheel 27 comprising a single marking working in conjunction with a capacitive sensor 28 which supplies a zero resetting signal for each revolution of the shaft 22, sent via connections 29 to the counting system 26.

The counting system 26 comprises means, not shown, for storing and selecting two numbers, for example between 0 and 500 if the number of markings on encoding disc 23 is 500.

A first switch 30 is capable of closing and opening when counting system 26 has reached the first preselected number. When switch 30 is closed the circuit comprising the relay 31 is also closed so that the said relay 31 is capable of closing contact 32 which is then kept closed through connection 33 and contact 34 which supplies electric current via connectios 35 to the control device of a first clutch 36 or low-speed clutch. Thus, when contact 34 is closed one of the phases (phase 1) of the power supply current is connected via connection 37 whilst the other phase (phase 2) is connected via connection 38 to the connections 35 of the clutch control 36.

The counting system 26 comprises a second switch 39 which is capable of closing and opening for the second preselected number in order to send a control pulse via connection 40 to the relay 41 which for a moment opens the normally-closed contact 42. The opening of contact 42 interrupts energization of relay 31 and opens the circuit holding contact 32. The same action causes contact 34 to change over from the position feeding the first low-speed clutch 36 to the position shown in FIG. 2 in which the control device of the second or high-speed clutch 43 is fed via connection 44.

A high-speed drive shaft 45 transmits its rotational torque via a bevel gear set 46 to an intermediate shaft 47 which can be connected alternately to two half-shafts 48 and 49 through the controlled clutches 36 and 43. The half-shaft 48 working with the low-speed clutch 36 carries a pinion 50 which meshes with a gear 51 fixed to shaft 10.

The half-shaft 49 working with the high-speed clutch 43 carries a wheel 52 which meshes with a pinion 53 fixed to shaft 10.

In these conditions operation of either of clutches 36, 43 changes the gear ratio of the transmission transmitting the rotational torque between the drive shaft 45 and the shaft 10 which carries the feed rollers 9a, 9b. Two different speeds of rotation are thus obtained for shaft 10.

Figure 3:
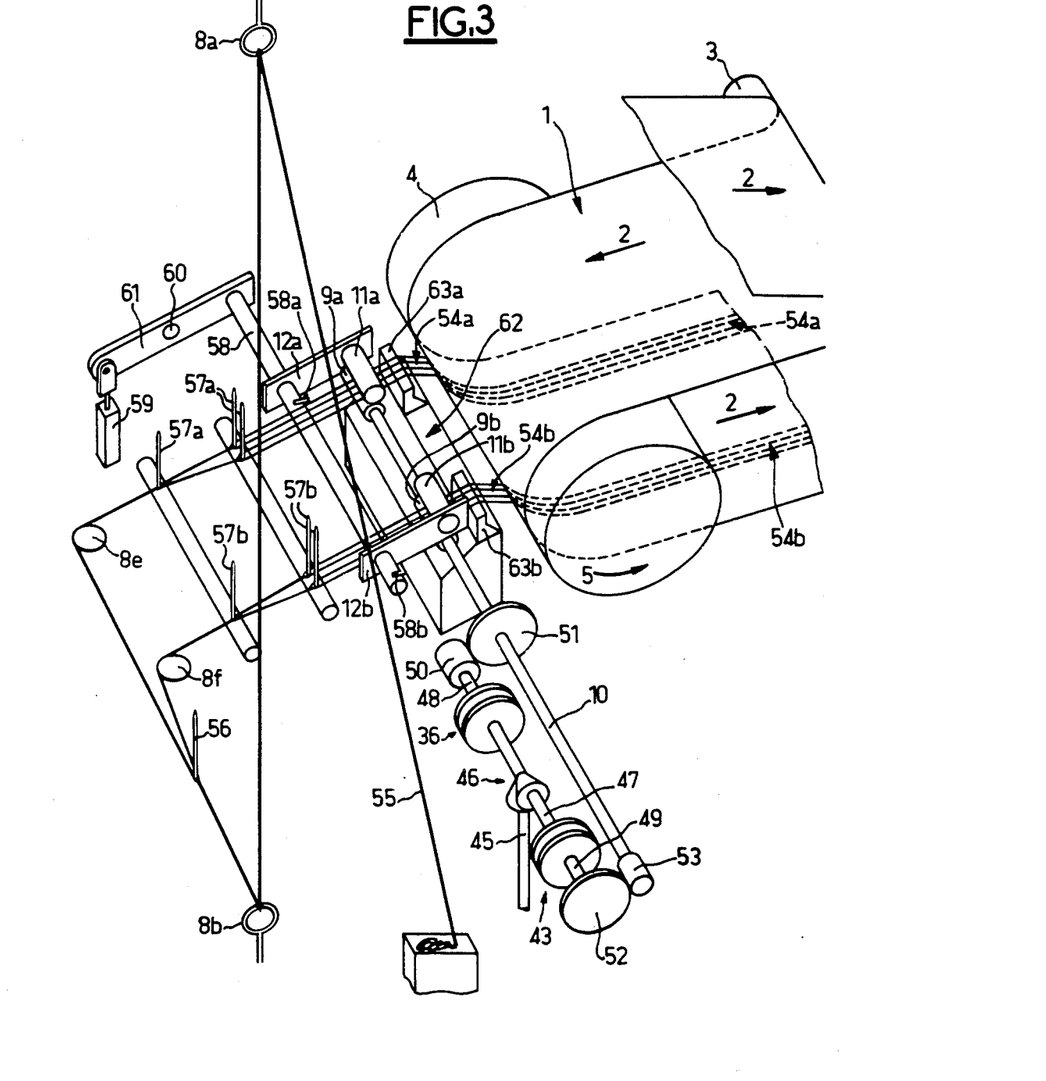
FIG. 3 is a schematic perspective view of a part of an installation variant which also enables the process of the invention to be applied and which is more especially suited for the application of a plurality of separate elastic strands.

In FIG. 3, in which the same components carry the same reference numbers, is illustrated an embodiment of the invention which is similar in principle to the embodiment illustrated in FIG. 1 but which uses, instead of the two elastic strips 7a, 7b, four individual strands 54a, 54b obtained from a single multi-strand tape 55 that undergoes a succession of separations by passing over the separating spikes 56, 57a, 57b placed in its path. In this embodiment we also find the feed rollers 9a, 9b driven at variable speed by the shaft 10. The levers 12a, 12b of the presser rollers 11a, 11b are here mounted to rotate freely on a transverse rod 58 which can be moved upwards by the action of a control cylinder 59 causing a lever 61 to pivot round its fixed pivot 60. Stops 58a, 58b fixed to the rod 58 limit the downwards pivoting movement of levers 12a, 12b. In this way the upwards movement of the rod 58 raises the levers 12a, 12b and the presser rollers 11a, 11b as soon as the levers 12a, 12b come into contact with the stops 58a, 58b. Continuation of the upward movement of the rod 58 lifts the individual strands 54a, 54b off their adhesive coating unit 63a, 63b during machine stoppages.

In this embodiment the adhesive coating operation is carried out by passing the individual strands 54a, 54b over two adhesive coating units 63a, 63b which comprise grooves designed for each individual strand to pass through, the said grooves being filled with high-temperature liquid adhesive (hot melt) so as to completely coat each individual strand when it passes through the said groove. Refer for further details on this adhesive coating method and on the use of multi-strand elastics to patent application No 83 00780 filed on Jan. 19, 1983 in this applicant's name.

The position shown in FIG. 3 of the feed rollers 9a, 9b driven in rotation at variable speed and placed just before the adhesive coating units 63a, 63b means that the same result is achieved as with the embodiment of FIG. 1, i.e. variable tension of the individual elastic strands 54a, 54b, which are also coated with adhesive continuously.

Figure 4:
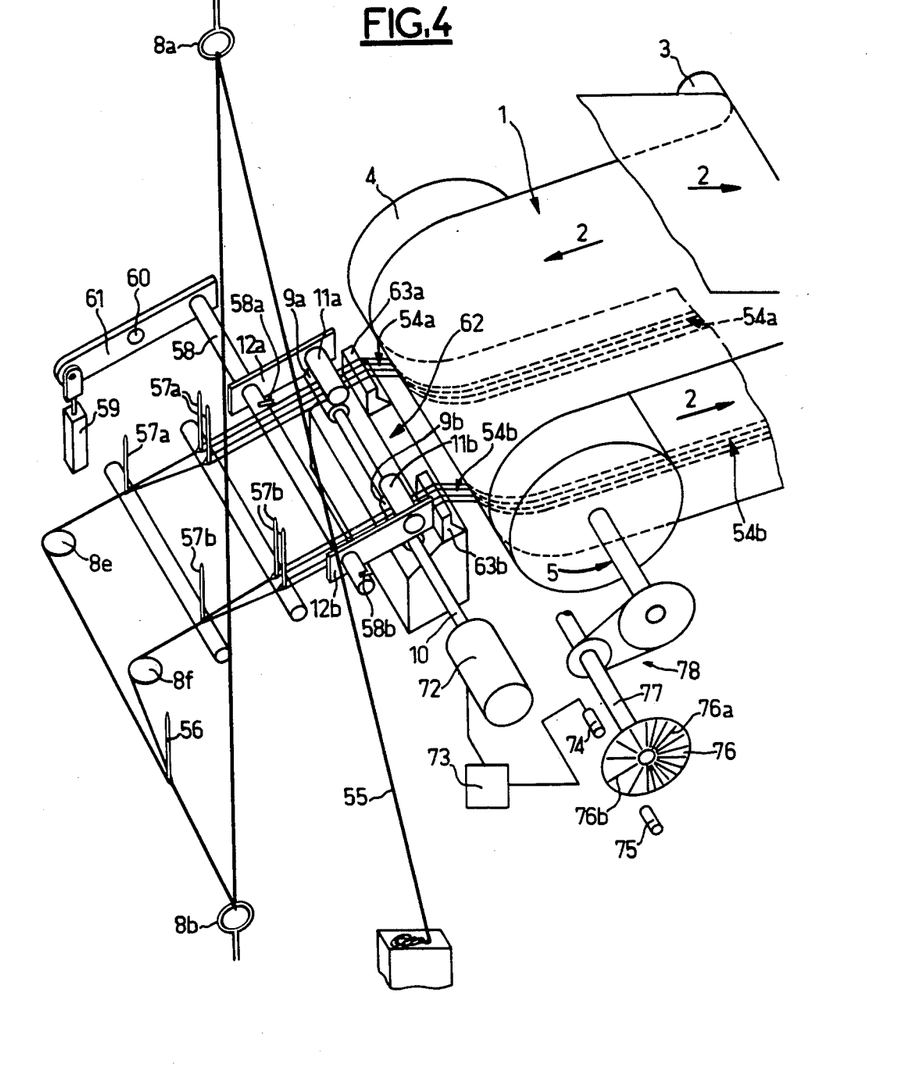
FIG. 4 is a schematic perspective view of the version of FIG. 3 showing a variant of the elastic tension change control.

In FIG. 4, which illustrates another version of the elastic tension variation control system, we find all the components of FIG. 3, except for the means of driving shaft 10 carrying the feed rollers 9a, 9b. The shaft 10 is here driven by an electric stepping motor 72 fed by a control circuit 73. The control circuit receives the pulses from a photoelectric receiver or sensor 74 illuminated by a source 75 through an encoding disc 76 having alternating transparent and opaque lines on it. The encoding disc 76 has round its periphery two segments 76a, 76b, one of which (76a) has the transparent lines closer together and the other of which (76b) has the transparent line spaced further apart. The encoding disc 76 is mounted on a shaft 77 which is coupled, for example by a chain drive as shown, with the drum 4 so that it makes a complete revolution when the drum makes a rotation which makes a length of sheet 1 corresponding to a diaper pass by. Furthermore, the number of transparent lines on the encoding disc 76 and the stepping motor 72 are selected so that the motor 72 makes one complete revolution for each revolution of the disc 76. Consequently the differently spaced lines on the encoding disc 76 driven at constant speed produce a periodical variation in the speed of the stepping motor 72 and of the feed rollers 9a, 9b and therefore in the tension of the elastic strands 54a, 54b.

Figure 5:
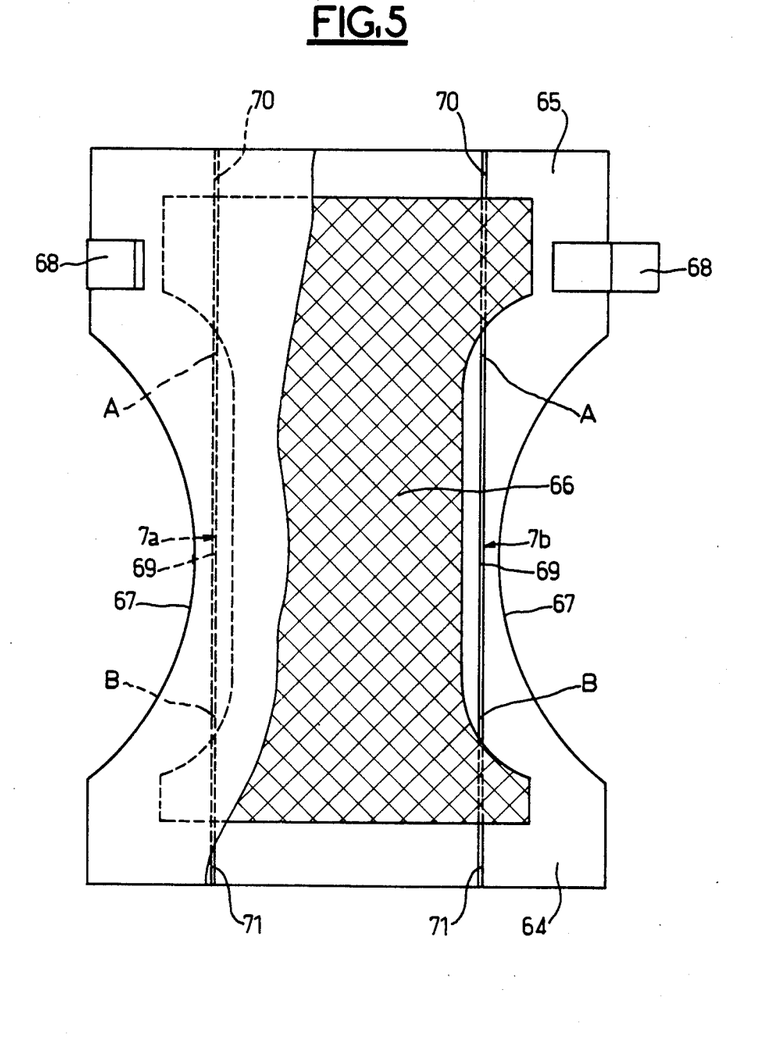
FIG. 5 is a partly cut away top view of a diaper according to the invention in the extended condition.

FIG. 5 shows a diaper produced by the process of the invention and shown in the extended position to simplify the drawing. We again have the impermeable sheet 1 and the elastic strips 7a, 7b. The impermeable outer envelope formed by the sheet 1 comprises a front transverse margin 64 and a back transverse margin 65. An absorbent pad is fixed on the inner face of sheet 1. Two round lateral cut-outs 76 allow the legs to pass through. Finally two adhesive fastenings 68 are fixed on the back margin 65 and allow the diaper to be closed.

As can be seen in FIG. 5 the two elastic strips 7a, 7b are fixed throughout their length along a straight line parallel to the longitudinal axis of the diaper. They comprise a middle portion 69 adhered with tension over the middle crotch zone between points A and B and two end portions 70 and 71 also adhered, but this time without tension, to the transverse margins 64 and 65.

It will be noted that the elastic strips 7a, 7b are fixed in the immediate proximity of the edges of the absorbent pad 66 in the crotch zone.

Although the description has been given in connection with the use of elastics laid along a straight line it will be understood that the invention could also apply without appreciable modification to laying curvilinear elastics coated with adhesive throughout their length and comprising portions of varying tension. In fact it would suffice to provide means of driving in cyclical transverse translation all the feed and adhesive-coating means working in conjunction with each elastic, without modifying the operation of these components as described. The point of contact of each elastic with the impermeable sheet would then be moved periodically, which would make the elastic adhere along a curvilinear path which could, for example, follow the contours of the rounded lateral crotch cut-outs.

Furthermore although, in the illustrated examples, the elastic feed speed comprises two preset values, it will be understood that the invention is not restricted to the use of two values. On the contrary it would be possible, without any big changes, to use more than two values, or even continuous variation, in order to obtain zones with varying tension for the adhered elastics making it possible, for example, to match the tension of each portion of elastic to the comfort and watertightness characteristics required for each portion of the diaper.

Finally, it goes without saying that the control of the change in tension of the elastic means could, instead of being derived from the rotational movement of the drum 4 over which the sheet 1 passes, be derived from any other rotary component making one revolution per article (diaper).

I claim:

1. A method for continuous manufacturing of disposable diapers comprising an outer impervious envelope having a longitudinal axis, front and back transverse margins, and a central crotch zone, an absorbent pad having the same longitudinal axis and secured inside said envelope, and elastic means disposed on both sides of said longitudinal axis, each comprising a plurality of individual elastic strands adhesively secured to said envelope, comprising the steps of:

(a) passing a continuous strip of impervious envelope material along a significant portion of the peripheral smooth surface of a rotary drum rotating about a fixed axis, said strip being free, during passage around said drum, of contact by pressure rolls and grips facing said drum, said surface being maintained at an adhesive setting temperature, (b) continuously feeding two arrays, each of a plurality of individual elastic strands, (c) periodically varying the feeding speed of said elastic strands from a first speed substantially equal to the speed of said continuous strip on said rotary drum to a second speed less than the speed of said continuous strip on said rotary drum, (d) passing said elastic strands into grooves open at their upper ends only filled with high temperature hotmelt adhesive material, (e) applying each said array of elastic strands as it comes from its groove with its hot adhesive material, without precooling, directly to the surface of said continuous strip, the two arrays being applied on opposite sides of said longitudinal axis while said strip is contacting said rotary drum and free from pressure rolls and grips, whereby immediate setting of the hotmelt adhesive carried by each strand is obtained at the drum, due to the drum's surface being at an adhesive setting temperature, and the strands are adhesively secured along their entire length to said continuous strip with some portions being elastically stretched and some portions substantially unstretched, and (f) applying and securing absorbent pads onto said continuous strip and severing transversely said strip and said elastic strands, whereby said elastically stretched portions of the elastic strands contract to gather the strip material to which it is secured in the crotch zone.

2. The method of claim 1 having the steps of:
obtaining each array of elastic strands by continuously separating a plurality of individual elastic strands from a multi-strand elastic tape and continuously coating each strand over its whole circumference with a liquid high-temperature adhesive.

3. The process of claim 1, including retaining the rotary drum at a temperature between 30° C. and 100° C., so as to produce immediate setting of the liquid adhesive carried by each said elastic strand.

4. The process of claim 1 comprising guiding said elastic strands between the place where they are coated adhesive and the drum, to bring them towards the drum.

5. The process of claim 2 wherein the step of continuously feeding the two arrays of strands is done by driving a rotary feed roller at variable speed and engaging the strands with a friction roller, which comes into contact with said feed roller by gravity.

6. The process of claim 1 wherein the step of feeding said two arrays is accomplished by two pairs of rollers, each pair comprising a feed roller, said feed rollers being mounted on a common shaft, and a friction roller urged by gravity toward and against its feed roller.

7. The process of claim 6 wherein the step of periodically varying the feeding speed is done by rotating a single drive shaft driving two gear trains with different drive ratios, and by alternately actuating a pair of controlled clutches releasably connecting each gear train to said common shaft.

8. The method of claim 7 comprising sensing the angular position of said rotary drum and supplying therefrom the control for the two clutches.

9. The method of claim 6 comprising driving the feed rollers by a stepping motor and wherein the step of periodically varying the speed is accomplished by controlling the stepping motor through driving at constant speed an encircling disc with photoelectric readout and having on its periphery two segments with different speed lines.

10. A method for continuous manufacturing of disposable diapers comprising an outer impervious envelope having a longitudinal axis, front and back transverse margins, and a central crotch zone, an absorbent pad having the same longitudinal axis and secured inside said envelope, and elastic means disposed on both sides of said longitudinal axis having a plurality of individual elastic strands adhesively secured to said envelope, comprising the steps of:

(a) passing a continuous strip of impervious envelope material along a significant portion of the peripheral smooth surface of a rotary drum rotating about a fixed axis, said strip being free, during passage around said drum, of contact by pressure rolls and grips facing said drum, said surface being maintained at an adhesive setting temperature of between about 30° C. and about 100° C., (b) continuously feeding two arrays, each comprising a plurality of individual elastic strands, between two pairs of rollers, each comprising a rotary feed roller driven at variable speed and a friction roller, (c) periodically varying the rotary speed of said rotary feed rollers from a first speed where the feeding speed of the elastic strands downstream from the pairs of rollers is substantially equal to the speed of said continuous strip on said rotary drum, to a second speed where the feeding speed of the elastic strands downstream from the pairs of rollers is less than the speed of said continuous strip on said rotary drum, (d) passing said elastic strands downstream from said pairs of rollers into grooves open at their upper ends only filled with high temperature hotmelt adhesive material, (e) applying each said elastic strand as it comes from its groove, with its adhesive material hot, without precooling, directly to the surface of said continuous strip, on opposite sides of said longitudinal axis while said strip is contacting said rotary drum and free from pressure rolls and grips, whereby immediate setting of the hotmelt adhesive carried by each strand is obtained at said drum due to the drum's surface being at an adhesive setting temperature, and the strands are adhesively secured along their entire length to said continuous strip, with some portions being elastically stretched and some portions substantially unstretched, and (f) applying and securing absorbent pads onto said continuous strip and severing transversely said strip and said elastic strands, whereby said elastically stretched portions of the elastic strands contract to gather the strip material to which it is secured in the crotch zone.

* * * * *

UNITED STATES PATENT AND TRADEMARK OFFICE
CERTIFICATE OF CORRECTION

PATENT NO. : 4,762,582
DATED : August 9, 1988
INVENTOR(S) : Raphael de Jonckheere It is certified that error appears in the above-identified patent and that said Letters Patent are hereby corrected as shown below:

Column 3, line 42, "continuousluy" should read
--continuously--.

Column 7, line 15, "cut-outs 76" should read
--cut-outs 67--.

Column 8, line 53, which is line 3 of claim 4,
before "adhesive" insert --with--.

Signed and Sealed this

Third Day of January, 1989

Attest:

DONALD J. QUIGG

*Attesting Officer*      *Commissioner of Patents and Trademarks*